(12) United States Patent
Fung et al.

(10) Patent No.: US 9,066,849 B2
(45) Date of Patent: Jun. 30, 2015

(54) PILLBOX, MEDICATION MANAGEMENT SYSTEM AND MEDICATION DISPENSING SYSTEM

(75) Inventors: Wai Tong Fung, Hong Kong (HK); Wai Ling Chan, Hong Kong (HK)

(73) Assignee: Wai Ling Chan, Hong Kong (HK)

( * ) Notice: Subject to any disclaimer, the term of this patent is extended or adjusted under 35 U.S.C. 154(b) by 0 days.

(21) Appl. No.: 14/234,537

(22) PCT Filed: Jul. 11, 2012

(86) PCT No.: PCT/CN2012/078473
§ 371 (c)(1),
(2), (4) Date: Jan. 23, 2014

(87) PCT Pub. No.: WO2014/008638
PCT Pub. Date: Jan. 16, 2014

(65) Prior Publication Data
US 2014/0166529 A1 Jun. 19, 2014

(51) Int. Cl.
*G08B 1/00* (2006.01)
*A61J 1/03* (2006.01)
(Continued)

(52) U.S. Cl.
CPC .... *A61J 1/03* (2013.01); *A61J 7/04* (2013.01);
(Continued)

(58) Field of Classification Search
CPC ............................. A61J 7/0481; G06F 19/3456
USPC ................... 340/309.16, 572.1–572.8, 573.1; 206/534, 539; 368/10
See application file for complete search history.

(56) References Cited

U.S. PATENT DOCUMENTS

| 4,793,492 | A | 12/1988 | Halbich |
| 6,169,707 | B1 * | 1/2001 | Newland ........................ 368/10 |
| 6,324,123 | B1 * | 11/2001 | Durso ............................. 368/10 |

(Continued)

FOREIGN PATENT DOCUMENTS

| CN | 2506253 | 8/2002 |
| CN | 2794509 | 7/2006 |
| CN | 200966769 | 10/2007 |

OTHER PUBLICATIONS

International Search Report for international application No. PCT/CN2012/078473, dated Apr. 18, 2013 (3 pages).

*Primary Examiner* — Tai T Nguyen
(74) *Attorney, Agent, or Firm* — Hamre, Schumann, Mueller & Larson, P.C.

(57) ABSTRACT

The invention provides a pillbox comprising a plurality of pill receiving compartments detachably connected with one another in side-by-side relation to form a unitary structure, each of the compartments being constructed to store pills to be taken at a single predetermined time and have an opening which is covered by a cover and through which 5 the compartment is accessible; wherein the unitary structure is configured such that the plurality of compartments are arranged sequentially according to a medication schedule created according to a prescription, with the compartment storing the pills to be taken first as an outermost one, and that only the opening of the outermost compartment is permitted to be uncovered all the time, and wherein the outermost compartment is removed from the 10 unitary structure after the pills contained therein are taken. The invention also provides a medication management system and a mediation dispensing system based on the pillbox.

29 Claims, 9 Drawing Sheets

(51) Int. Cl.
*A61J 7/04* (2006.01)
*G06F 19/00* (2011.01)

(52) U.S. Cl.
CPC ........ *A61J 7/0481* (2013.01); *A61J 2007/0436* (2013.01); *A61J 2200/30* (2013.01); *A61J 2200/60* (2013.01); *A61J 2200/70* (2013.01); *G06F 19/3456* (2013.01); *G06F 19/3462* (2013.01)

(56) References Cited

U.S. PATENT DOCUMENTS

| | | |
|---|---|---|
| 7,387,207 B2 | 6/2008 | Priebe et al. |
| 7,978,564 B2 | 7/2011 | De La Huerga |
| 8,193,918 B1 | 6/2012 | Shavelsky et al. |
| 2010/0314282 A1 | 12/2010 | Bowers |

* cited by examiner

PILLBOX, MEDICATION MANAGEMENT SYSTEM AND MEDICATION DISPENSING SYSTEM

FIELD OF THE INVENTION

The present invention is generally related to the field of medication management system. More specifically, the present invention concerns a pillbox for monitoring and improving medication compliance and decreasing medication mismanagement by increasing the simplicity of patient self-administration, and to a medication management system and a medication dispensing system based on the pillbox of the invention.

BACKGROUND OF THE INVENTION

Physicians are trained to diagnose a disease and select an appropriate medication based on pharmacokinetic and pharmacodynamic properties. However, even the most carefully chosen and optimal medication cannot work if the patient does not take it appropriately. Medication compliance, an essential component of a successful health outcome, is largely in the domain of the patient. The responsibility for fulfillment of the prescribed regimen lies with the patient.

As the population ages, and as people anticipate living longer since they live healthy and vigorous lives well, the people have become increasingly reliant on medications. However, as more people take more medicines, the opportunities for non-compliance, for over-taking or under-taking medicines or for mixing drugs that result in negative outcomes and even serious consequences to the patient's health, increase. Until now, no monitor system provides the accurate medicine from the pharmaceutical factories to the patients. One of the reasons is that the patients are always confused about what, where and when the set of pills to be administrated. It is quite difficult to monitor whether the patients take the correct pills on time.

In order to solve this problem, attempts have been made to provide various forms of apparatuses and systems to assure that the patients are taking their medications as prescribed. Generally, there are two methods of using the labels and the sensors, for example, based on IR, magnet technologies or the like to distinguish each slot of the pills corresponding to the medication schedule. The method of using the labels is very low cost, but the elderly is easy to make the mistakes and increase the non-compliance. The second method of using the sensors is only capable of monitoring whether the door of the pill slot is opened or not, and also is very expensive and has the drawbacks of portable inconvenience and high power consumption.

The specific apparatuses and systems increasing and/or monitoring the medication compliance may be known from U.S. Pat. Nos. 7,978,564B2, 8,193,918B1 and US2010/0314282A1, for example.

The U.S. Pat. No. 7,978,564B2 relates to an interactive medication container or console that holds or organizes one or more medication vials or containers. Each vial has a memory strip containing mediation and prescription information, and also a reminder unit that is attached to and portable with the individual vials. The console or reminder unit reads the information strip of the vial and communicates this information to or interacts with the patients to remind them to take the medication. The system disclosed in the patent is very structurally complicated and expensive.

The U.S. Pat. No. 8,193,918B1 issued to Eran Shavelsky et al discloses an interactive medication dispensing system comprising a body including a bottom housing and a top bezel movably securing over the bottom housing, a plurality of cups received in the respective orifices of the bottom housing to store the pills taken by the user at a single corresponding predetermined time, an on-board processor for the treatment schedule, and a server for transmission of alerts. This system integrate the pills into one housing according to the treatment schedule, and monitors the compliance by determining when an indicated cup is accessed, based upon at least one of manipulating a lid and/or placing into, removing from or replacing into the correct orifice based upon the indication. Since all the cups are accessible, errors of taking the wrong pills can be introduced. Also, the configuration of this system is complex.

The US patent application no. 2010/0314282A1 relates to a pill organizer comprising a plurality of units for containing pills and coupled to each other via a connection means, for example a peg and a slot, or a rail and a track. The rows and the columns of the pill organizer correspond to the days of the week and the time of the day, respectively. The units can attach and detach from one another, thereby creating a custom-tailored pill organizer. Again, this pill organizer may not assure the patients to take the right medication, since all the units are accessible.

Therefore, there is a need for a pillbox which allows the patients to take the right medication, at the right time, on the right day, at the right dose, no matter where the patients are. There is another need for a pillbox which enhances medication compliance and reduces adverse drug reactions in a cost-effective way.

SUMMARY OF THE INVENTION

The present invention has been developed to fulfill the needs noted above and therefore has a principle object of the provision of a pillbox, which offers a mechanism to take the right medication, at the right time, on the right day, because of the innovative structural design incorporating the RFID (Radio Frequency Identification) technology to identify and keep track of the medication records.

Another object of the invention is to provide a pillbox which helps decrease medication mismanagement by increasing the simplicity of patient self-administration, thereby enhancing the ease and convenience of taking the medication and improving the compliance.

These and other objects and advantages of the invention are satisfied by providing a pillbox comprising a plurality of pill receiving compartments detachably connected with one another in side-by-side relation to form a unitary structure, each of the compartments being constructed to store pills to be taken at a single predetermined time and have an opening which is covered by a cover and through which the compartment is accessible; wherein the unitary structure is configured such that the plurality of compartments are arranged sequentially according to a medication schedule created according to a prescription for a particular patient, with the compartment storing the pills to be taken first as an outermost one, and that only the opening of the outermost compartment is permitted to be uncovered all the time, and wherein the outermost compartment is removed from the unitary structure after the pills contained therein are taken.

The term "outermost compartment" herein refers to a compartment of the unitary structure (i.e. the pillbox) for storing the pills to be taken first by the patient, which is arranged at the outer end of the unitary structure and can be assessable by opening its cover.

In one embodiment of the invention, the compartment is constructed to have an opened top as the opening, a bottom, and side walls, and comprise an actuator for opening the cover and mounted on the side wall where the compartment is connected to the preceding compartment; and the cover is pivotally and openably locked to the compartment.

Preferably, each of the compartments has at least one longitudinal guiding bulge or at least one longitudinal guiding slot on the side wall where the compartment is connected to the preceding compartment and on the opposite wall thereof, respectively, and at least one longitudinal guiding slot or at least one longitudinal guiding bulge on the other two side walls, respectively, so that the guiding bulge is vertically inserted into and engages with the guiding slot to enable the connection of the adjacent two compartments.

In another embodiment of the invention, the compartment is constructed to have a closed top, a bottom and side walls, with the opening formed in the side wall where the compartment is connected to the preceding compartment; and the cover is provided as a hinged side door to cover the opening.

In order to identify the compartment and keep track of the medication records, each of the compartments is provided at its bottom with a radio frequency identification (RFID) tag for containing and updating data associated with the pillbox, and the pillbox further comprises a microcontroller unit (MCU) with a RFID reader to process and read the data contained in the RFID tag. The data associated with the pillbox may include the ID number assigned to the respective compartment, personal data of the patient, the prescription for the patient, the medication schedule, a time when the patient is to take the pills, a time when a reminder alert is sent to the patient, and pill information including manufacturers and availability of the pills. In one embodiment of the invention, the MCU is configured to generate the reminder alert indicating the time when the patient is to take the pills, upon reading the RFID tag of the removed compartment in which the pills have been taken.

Preferably, the pillbox further comprises a LED indicator, an acoustic output unit, a vibration motor, or any combination thereof, operably connected to the MCU for indicating the time for the taking of the pills as a reminder alert indication sent to the patient.

For the sake of clarity, the plurality of the compartments each is assigned with a corresponding ID number for the purpose of identification of the compartments, and a liquid crystal display operably connected to the MCU is provided to indicate the time for the taking of the pills by the patient and indicating the corresponding number of the compartment in which the pills are to be taken.

In a second aspect of the invention, there is provided a medication management system, comprising:

a pillbox of the invention discussed above; and a server which contains data associated with the pillbox and is accessible via wired or wireless connection by interested parties (for example the patients, the pharmacies, the doctors and the pharmaceutical factories).

A third aspect of the invention provides a medication dispensing system, comprising:

a pillbox of the invention discussed above; and a dispensing machine for dispensing the pills into the plurality of compartments according to the medication schedule and verifying the sequence of the plurality of compartments to construct the pillbox.

The dispensing machine may comprise a microcontroller unit (MCU) with a RFID reader for reading and updating the data associated with the pillbox and identifying the plurality of compartments and pill containers from the pharmaceutical factories; a communication module connected to the MCU to enable access to the dispensing machine; and a dispensing mechanism connected to the MCU for verifying and dispensing the pills from the pill containers into the plurality compartments through the RFID reader.

The medication dispensing system may also further comprise a server which contains data associated with the pillbox and is accessible via wired or wireless connection by interested parties (for example the patients, the pharmacies, the doctors and the pharmaceutical factories).

Unlike the prior art pillboxes or medication supporting apparatuses, the pillbox of the invention are characterized by providing the mechanism to ensure that only the outermost compartment is accessible all the time, while the other compartments arranged in sequential order are inaccessible, because the cover of each compartment will be opened only when its preceding compartment is detached from the pillbox. Every time the patient has taken the pills in the outermost compartment, he shall detach this empty compartment from the pillbox, such that the next compartment will become the outermost one. This would be repeated until all the pills in the pillbox are taken by the patient. With such unique design, the medication mismanagement when the patient self-administration is needed will be decreased.

The compartments for storing the pills can attach to and detach from one another, so a custom-tailored pillbox may be formed for the particular patient according the medication schedule. The empty compartments detached from the pillbox may be collected and recycled to construct a new pillbox by for example the pharmacies or the hospitals. In addition, the removal of the compartment indicates the achievement of the medication schedule.

The invention takes advantage of the RFID technology in the design of the pillbox. The pillbox is provided with a MCU with a RFID reader to store the data including the patient name and health conditions, the doctor's prescription, the doctor's remarks, the medication schedule generated according to the prescription, the manufacturers, sources and/or availability of the pills, the reminder alerts created according to the medication schedule, and the like. The RFID tab attached to the bottom of each compartment of the pillbox allows the compartment to be identified after it is read by the RFID reader. The MCU enables to send the reminder alerts to the patient at the prescribed time.

The medication management system and the medication dispensing system comprising the pillbox of the invention provide a new platform for dispensing supply chain management of pills and allow the interested parties including pharmaceutical factories, hospitals or clinics, pharmacies and patients to access, update and monitor the medication compliance and the pill availability via wired or wireless connection, for instance, by using smart phones and internet services.

The objects, characteristics, advantages and technical effects of the invention will be further elaborated in the following description of the concepts and structures of the invention with reference to the accompanying drawings.

BRIEF DESCRIPTION OF THE DRAWINGS

FIG. 11 b is a perspective view of the pillbox of FIG. 11a.

DETAILED DESCRIPTION OF THE INVENTION

Figure 1:
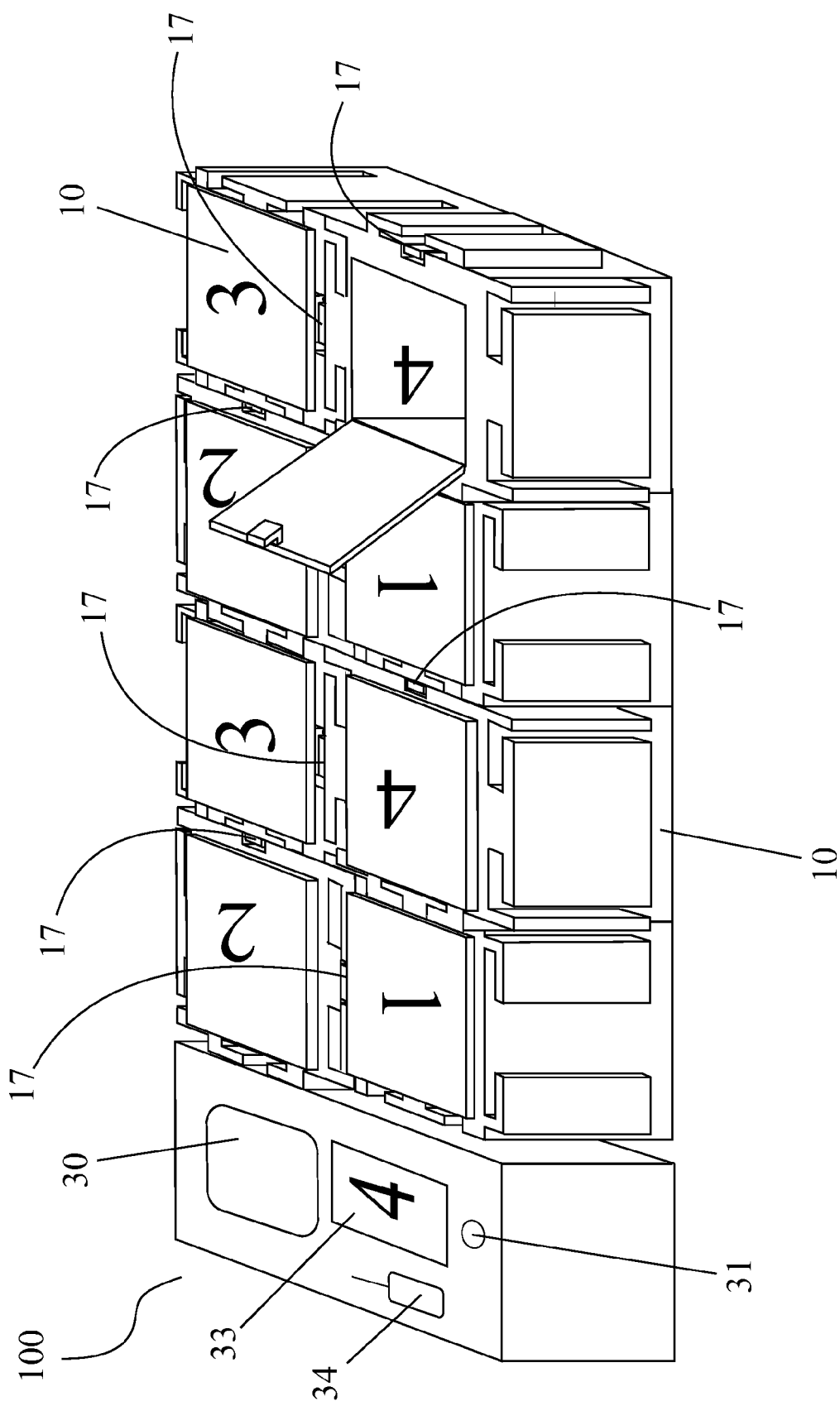
FIG. 1 is a perspective view of a pillbox comprising a plurality of compartments constructed according to a first embodiment of the invention.

While this invention is illustrated and described in preferred embodiments, the pillbox may be produced in many different configurations, sizes, forms and materials.

The inventive concept of the invention is that the pillbox is constructed by detachably assembling a plurality of compartments storing all the pills that are taken at a single determined time in sequential order according the prescribed medication schedule, while only the outermost compartment can be accessed and the other compartments are accessible only after the respective preceding compartments are removed. This ensures the right medication for the patient self-administration. This pillbox in combination with the RFID technology ensures to improve and trace the medication compliance.

Referring now to the drawings, FIGS. 1 to 10 provide a pillbox 100 constructed consistent with a preferred first embodiment of the invention. In this embodiment, the pillbox comprises 2×4 compartments 10 for the two days of administration regimen with four administrations each day. These compartments 10 are detachably connected with one another in side-by-side relation to form a unitary structure and arranged in a sequential order according to the medication schedule.

As shown in FIG. 1, all the compartments 10 have a same structure of same dimension. In this embodiment, the compartments 10 are of cubic configuration. Each compartment 10 is sized to store the pills to be taken at a single predetermined time and for the convenience, assigned with a corresponding number as shown in FIG. 1. The right four compartments in FIG. 1 store the pills to be taken in the first day, and the outermost compartment is assigned with the number "4" in which the pills will be taken first by the patient. After the taking of the pills, the patient must detach the no. 4 compartment from the pillbox, so that the no. 3 compartment becomes the outermost one of the pillbox and can be accessible. The left four compartments in FIG. 1 store the pills to be taken in the second day, and the no. 4 compartment of the second day would becomes the outermost one of the pillbox after the right four compartments have been removed. This way ensures the patient to take the right medication at the right time.

Figure 3:
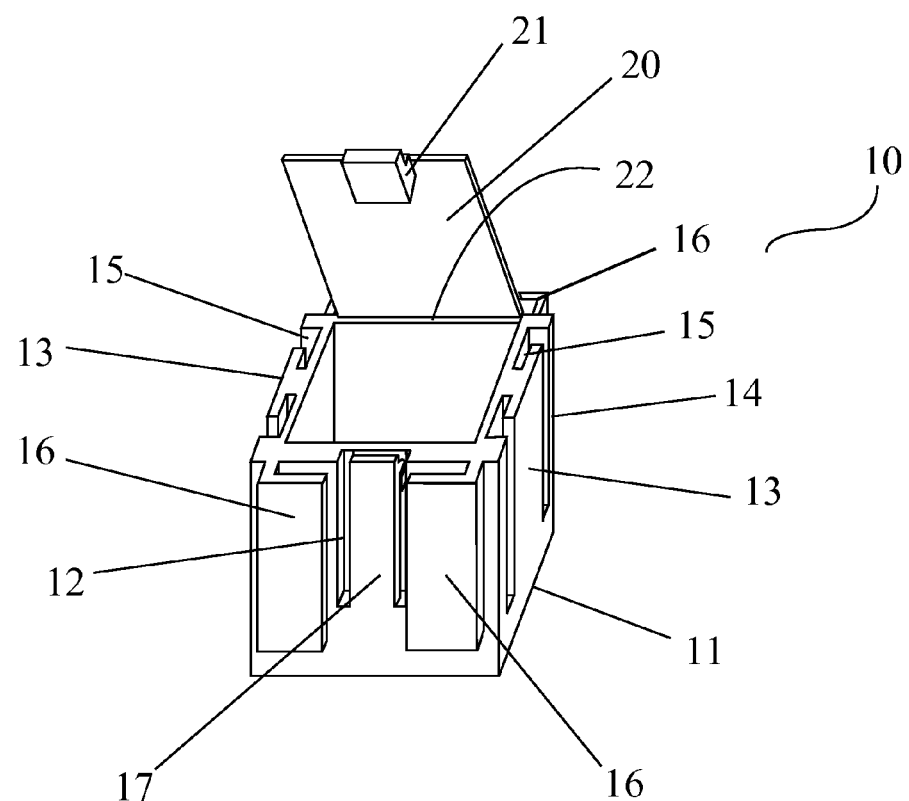
FIG. 3 is a perspective view of one compartment of the pillbox of FIG. 1.

As clearly illustrated in FIG. 3, the compartment 10 has a bottom 11, a front side wall 12, two opposite left and right walls 13, and a rear side wall 14 to define a chamber for storing the pills. The compartment 10 further has an opened top through which the pills are accessible. On the opposite side walls 13 are formed two spaced longitudinal guiding slots 15, respectively. The guiding slots 15 on each of the walls are positionally corresponding to two spaced longitudinal guiding bulges 16 formed on the front side wall 12 or the rear side wall 14, respectively. It is clear from FIG. 1 that the bulges 16 on the front side wall 12 of the no. 3 compartment slide into the slots 15 on the right side wall 13 of the no. 4 compartment to enable the detachable engagement of the two compartments; the bulges 16 on the front side wall 12 of the no. 2 compartment slide into the slots 15 on the left side wall 13 of the no. 3 compartment to enable the detachable engagement of the two compartments; and the bulges 16 on the front side wall 12 of the no. 1 compartment slide into the slots 15 on the left side wall 13 of the no. 2 compartment to enable the detachable engagement of the two compartments. In this way, the eight compartments 10 are connected from one another to form the pillbox 100 as an unitary structure. Removal of the compartment from the pillbox 100 may be achieved by simply sliding the bulges 16 out of the slots 15.

Figure 4:
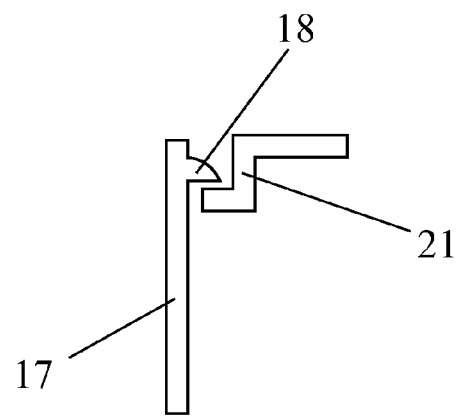
FIG. 4 is an enlarged view of an actuator for opening the cover of the compartment of FIG. 3.
Figure 5:
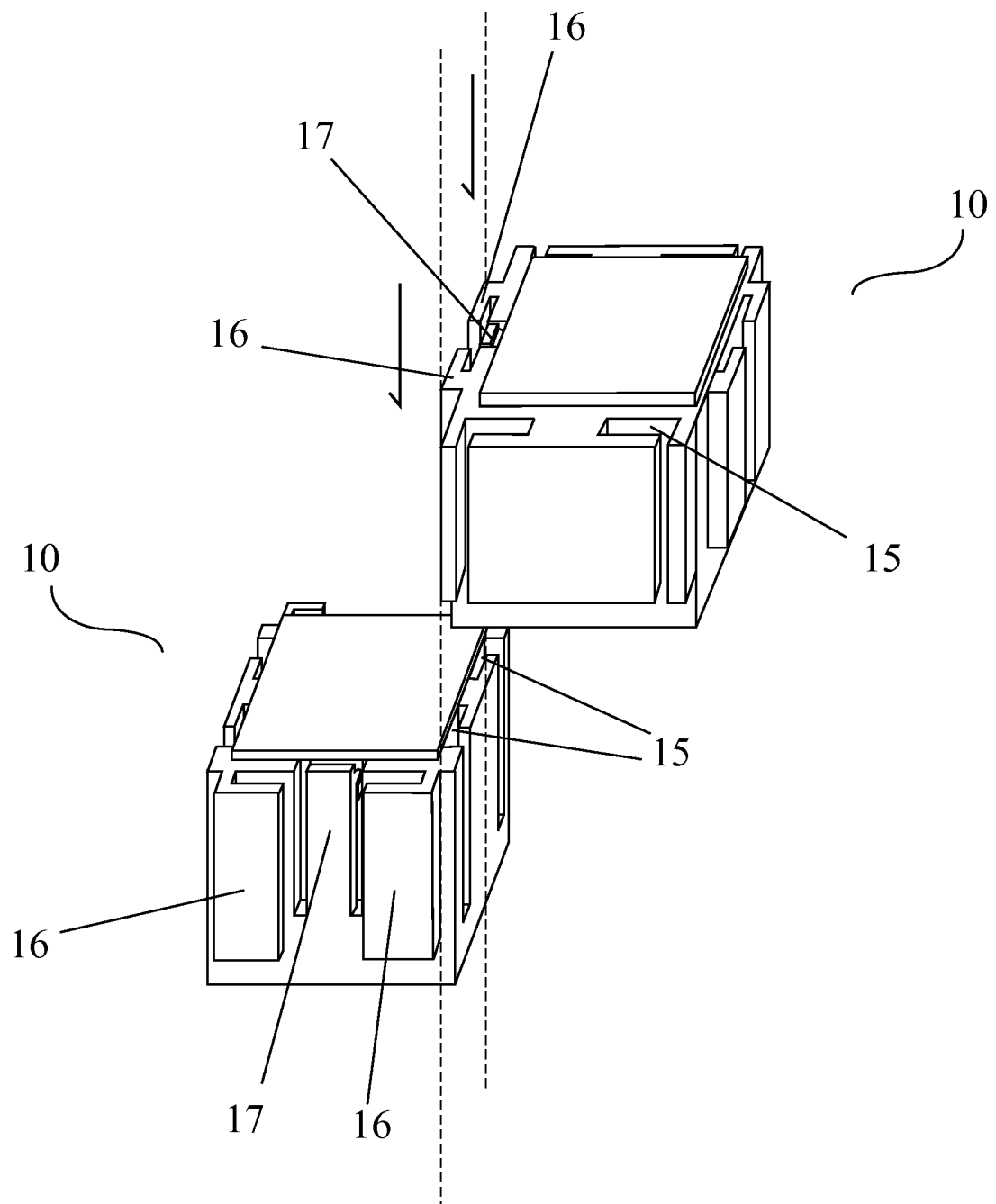
FIG. 5 is a schematic view of the ready-to-be-connected adjacent two compartments of the pillbox of FIG. 1.

A cover 20 is pivotally connected to the top of the rear side wall 14 by a hinge 22 to snugly cover the opened top of the compartment. As illustrated in FIG. 4, the cover 20 has a L-shaped flange 21 situated at the opposite side thereof to the hinge 22. A plate beam 17 having a protrusion 18 is formed on the front side wall 12 of the compartment 10. The protrusion 18 engages the L-shaped flange 21 of the cover 20 when the cover is assembled with the compartment, and such an engagement is designed to prevent the cover from being opened. The free end of the plate beam 17 may be forcibly pulled outward so that the protrusion 18 disengage from the L-shaped flange 21 to allow for the cover 10 to be opened. This locking cover arrangement provides an economical and effective arrangement for securing the cover 10 over the opened top of the compartment, while permitting to open the cover 10 only when the compartment in front of this compartment in question is removed.

The cover may be made from a transparent material for example PC (Polycarbonate) or ABS (Acrylonitrile-Butadene-Styrene) plastics, so that the pills stored in the compartment are visible. The plate beam 17 may be formed with an elastic material for example Polypropylene (PP). The plate beam 17 may be formed with a same or different material of the body of the compartment.

In order to manage and send automated reminder alerts to the patient, the pillbox 100 may further comprises a MCU 30 with a RFID reader, a LED indicator 31, an acoustic output unit 32, a liquid crystal display (LCD) 33 and a vibration motor 34, which are configured and arranged as shown in FIGS. 6 to 10, respectively. It would be understood that the LED indicator 31, the LCD 33 and vibration motor are optional and may be removed according to the actual needs and arrangements. The reminder alert can be indicated by continuous flash of the LED indicator 31, and/or vibration caused by the vibration motor 32, and/or beep sounds made by the acoustic output unit 32. The reminder alert may also be in the form of text message or voice message that is sent to the patient's mobile phone, indicating what pills shall be taken, when and any special instructions. In some cases, the text message or voice message may be sent by connecting the MCU of the pillbox to other peripherals, for example USB cable, via RF technologies. Of course, preferably the alert is sent to the patient at least a couple of minutes before the pills are to be taken. It would be understood that the LED indicator 31, the LCD 33 and vibration motor are optional and may be removed according to the actual needs and arrangements.

Figure 2:
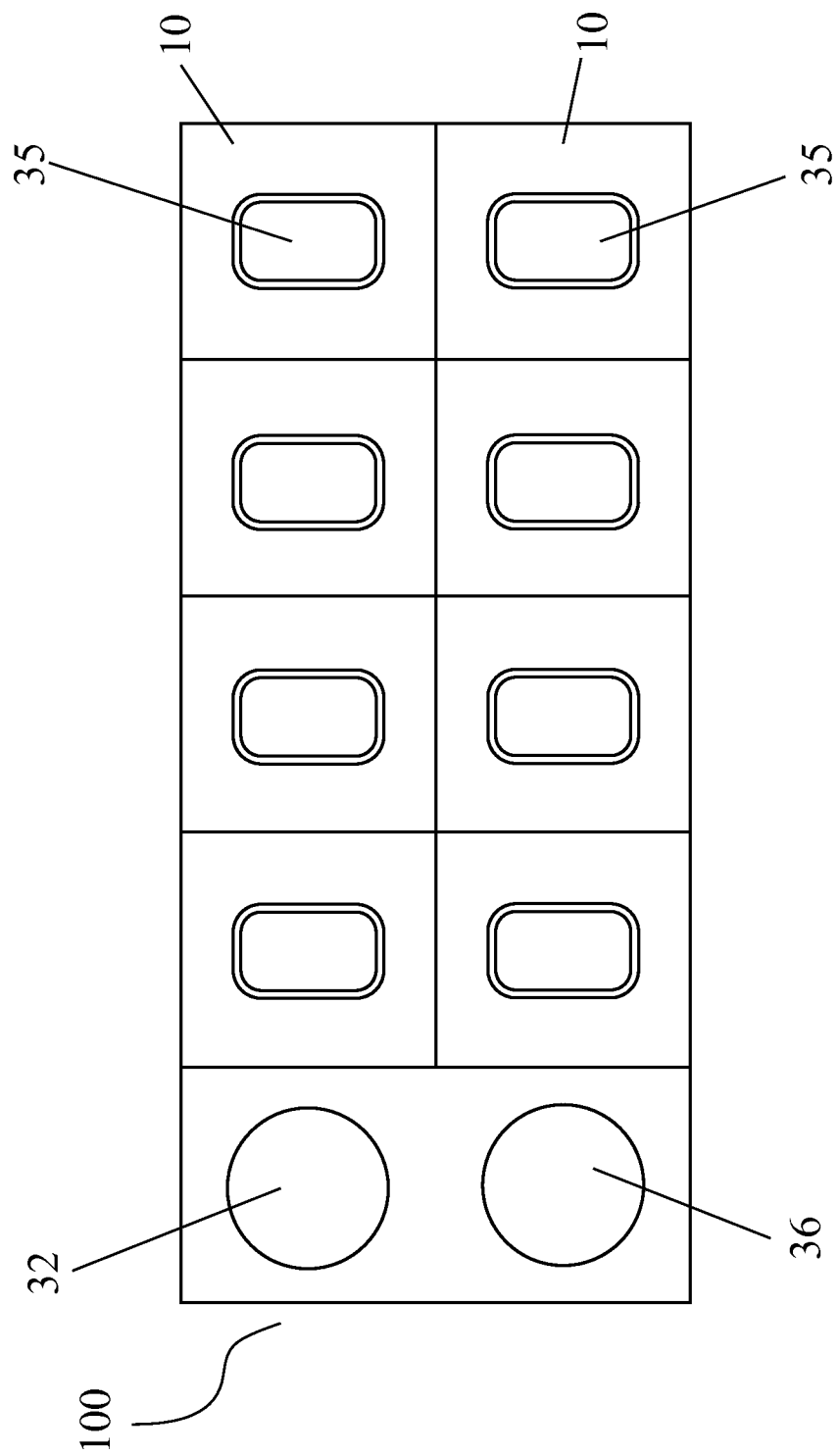
FIG. 2 is a bottom view of the pillbox of FIG. 1

One of the novel features of the invention is that a RFID tag 35 is attached to the bottom of each compartment 10 (see FIG. 2). The RFID tag 35 contains and updates the data associated with the pillbox including the ID number of the respective compartment. The data associated with the pillbox also includes personal data of the patient, the prescription for the patient, and the medication schedule generated according to the prescription, any special instructions specific to the patient, such as whether to take the medication before or after a meal, and/or whether the medication should be taken certain foods or liquids, etc. The RFID tag 35 may also contain the information on the manufacturers and availability of the pills. It would be appreciated that the RFID reader of the MCU 30 can store the data associated with the pillbox too.

In some cases, the RFID tag 35 may store the number of the respective compartment only and all the data associated with the pillbox is stored in the RFID reader of the MCU 30. After the number of the respective compartment is read by the RFID reader, all the data associated with the pillbox is accessible and displayed.

The following Table 1 is an example of the prescription including the types of the pills and administration regimen.

TABLE 1

| Patient Name | Chan Tai Man | I.D. | A123456B |
|---|---|---|---|
| Input Record | < 1 2 3 4 > Last New | | |
| Digital Prescription | < 1 2 3 4 > Last | | |

| | | | | Time slot (Day) | | | | |
|---|---|---|---|---|---|---|---|---|
| No. | Pill Type | Pill ID | Schedule | Period | Times | Total Day | Total PCS | Remarks |
| 1 | ABC | 387A | Hourly | 4 | 4 | 2 | 8 | None |
| 2 | DEF | 3451 | Hourly | 4 | 4 | 2 | 8 | In the morning |
| 3 | GHI | 1243 | Hourly | 3 | 4 | 2 | 8 | To be chewed |
| 4 | JKL | 4385 | Daily | 1 | 1 | 2 | 2 | For fever |
| 5 | MNO | 71A9 | Alternative Day | | | | | For bowel collie Dizziness |
| 6 | PQR | 248C | Weekly | | | | | Before/After food For vomiting At bed time To be sucked |
| . | . | . | | | | | | |
| . | . | . | | | | | | |
| . | . | . | | | | | | |
| N | XYZ | 3847 | Monthly | | | | | When required |
| | Input | Auto Gen. | Input | Input | Input | Input | Auto Gen. | For diarrhoea |

| Total No. of compartments: | 14 |
| Total No. of Pill Type: | 4 |
| Total No. of Pills: | 26 |
| Total No. of Day: | 2 |
| Doctor Name Signature | Pre-set |
| Organization | Pre-set |
| Date | Auto-Gen. |

The following Table 2 is an example of the medication schedule including the administration time of each pill.

TABLE 2

| Patient Name | | Chan Tai Man | I.D. | A123456B | | | | | |
|---|---|---|---|---|---|---|---|---|---|
| Compartment | | | | | | | Scheduled Medicine Time | | Actual Medicine |
| | ID | Pill Name or ID | | | | After | Finished | | |
| Sequence | No. | ABC | DEF | GHI | JKL | Hour | Yes/No | Scheduled | Shifted | Time |
| The First Day (20 Jun. 2012) | | | | | | | | | | |
| 1 | 4 | 1 | 2 | 1 | 1 | Starting time | Yes | 10:20 | N/A | 10:20 |
| 2 | 3 | 1 | 2 | 1 | 0 | 4 | Yes | 14:20 | 14:20 | 14:50 |
| 3 | 2 | 1 | 2 | 1 | 0 | 4 | Yes | 18:20 | 18:50* | 19:05 |
| 4 | 1 | 1 | 2 | 1 | 0 | 4 | Yes | 22:20 | 23:05 | 23:05 |
| The Second Day (21 Jun. 2012) | | | | | | | | | | |
| 1 | 4 | 1 | 2 | 1 | 1 | Starting time | No | 9:00 | N/A | 10:00 |
| 2 | 3 | 1 | 2 | 1 | 0 | 4 | No | 13:00 | 14:00 | 14:00 |

TABLE 2-continued

| 3 | 2 | 1 | 2 | 1 | 0 | 4 | No | 17:00 | 18:00 | 17:10 |
| 4 | 1 | 1 | 2 | 1 | 0 | 4 | No | 21:00 | 21:10* | 21:10 |

*The MCU is able to accumulate the time per pill if the actual administration time of the pills is delayed or ahead of the scheduled time.

In this embodiment, the MCU 30 is configured to generate the next reminder alert indicating a time when the patient is to take the pills, every time the patient places the empty compartment which has been removed after the taking of the pills to the RFID reader for reading. The MCU 30 would send the next reminder alert to the patient at the predetermined time as determined by the medication schedule and the LCD 34 will display the ID number of the compartment to be opened in order to further assure the right medication. This also enables to keep track of the medication compliance for the particular patient.

It should be noted that the patient may check and verify the data about the outermost compartment through reading the RFID tag 35 of the compartment by the RFID reader of the MCU 30, before the pills stored in the outermost compartment are taken. To perform this, the patient may remove the outermost compartment from the unitary structure and place its RFID tag on the RFID reader, and re-attach the compartment to the unitary structure after the reading is done.

Figure 6:
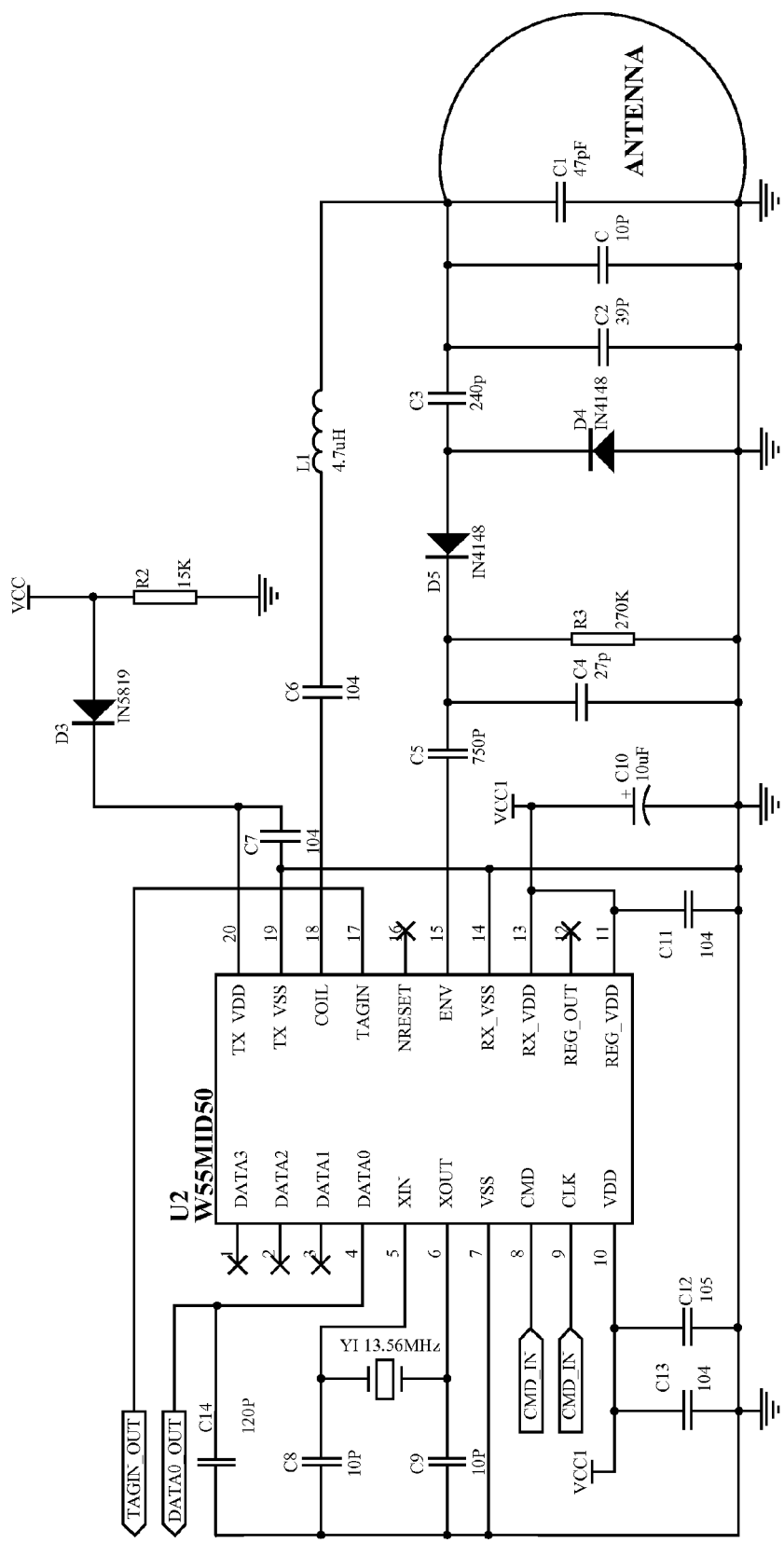
FIG. 6 is a circuitry of a MCU with a RFID reader used in the pillbox of FIG. 1.

FIG. 6 is a circuitry of MCU 30 of the pillbox of the invention. The MCU 30 comprises a microcontroller integrated circuit W55MID50 which is a flash 10 bits electrically-erasable programmable read-only memory (EEPROM), and associated peripheral circuits. The MCU 30 has respective pins connected to the LED indicator 31, the acoustic output unit 32, the liquid crystal display (LCD) 33 and the vibration motor 34 to enable them to indicate the reminder alert at the predetermined time. The LCD 33 may display the ID number of the to-be-handled compartment (see FIG. 1). The MCU 30 also has a RFID reader with the antenna for reading the RFID tag 35 of the compartment and then generates the reminder alert and updates the data of the medication records.

Figure 7:
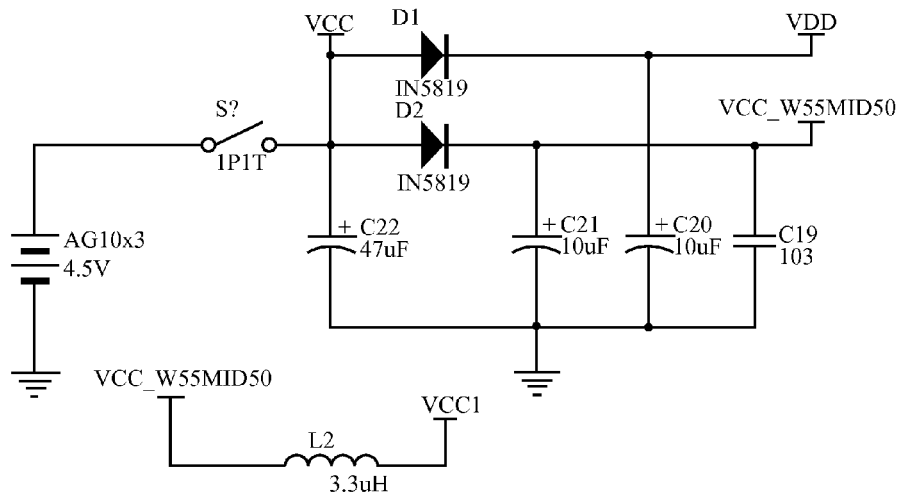
FIG. 7 is a circuitry of a power supply unit of the pillbox of FIG. 1.

FIG. 7 is a circuitry of a power supply unit of the pillbox 100 which are arranged at the bottom of the pillbox. The power supply unit is electrically coupled to the batteries 36 which are arranged at the bottom of the pillbox shown in FIG. 2 for powering the components, especially the integrated circuits.

Figure 8:
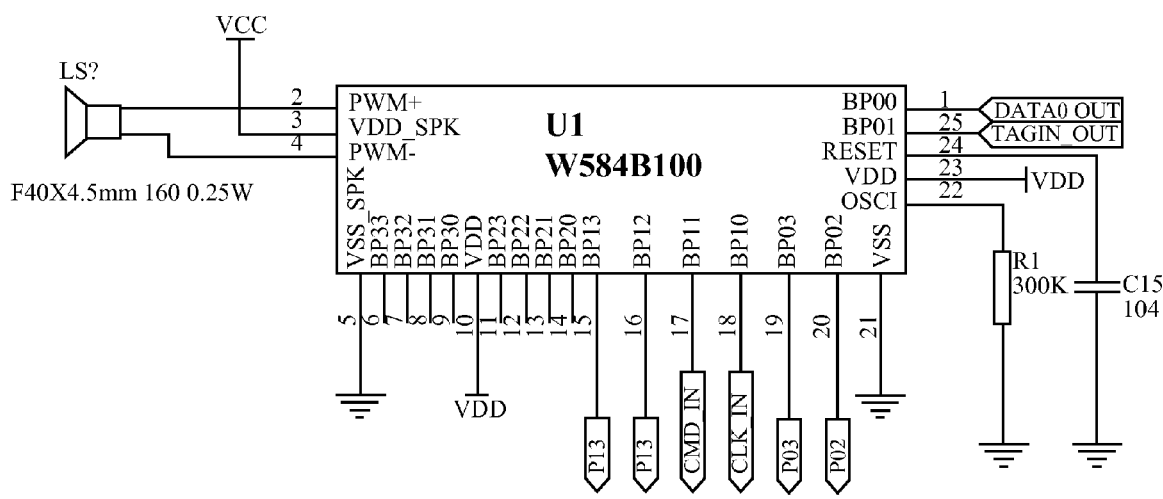
FIG. 8 is a circuitry of an acoustic output unit of the pillbox of FIG. 1.

FIG. 8 is a circuitry of the acoustic output unit 32 of the pillbox 100, which can be powered on by the batteries directly. The acoustic output 32 comprises a beeper or a speaker connected to the MCU 30 to make beep sounds, indicative of the time for the taking of the pills. The acoustic alert may be presented as music, voice or speech.

Figure 9:
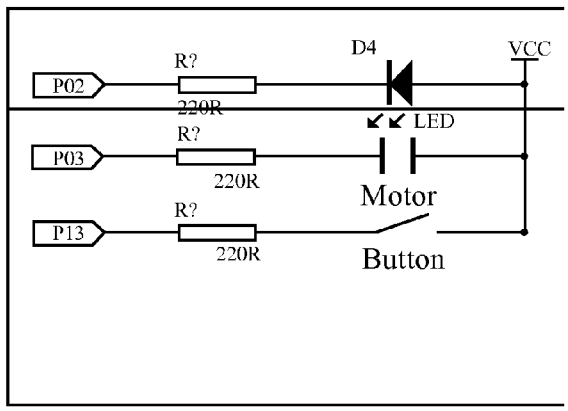
FIG. 9 is a circuitry of a LED indicator and a vibration motor of the pillbox of FIG. 1.

FIG. 9 is a circuitry of the LED indicator 31 and the vibration motor 34 of the pillbox 100, which may be powered on by the batteries directly. The LED indicator 31 has an input terminal connected to the pin 2 of the MCU 30 (which is a LED signal output terminal) for indicating the time for the taking of the pills. The vibration motor has an input terminal connected to the pin 3 of the MCU 30 to cause the vibration of the pillbox to alert the patient.

Figure 10:
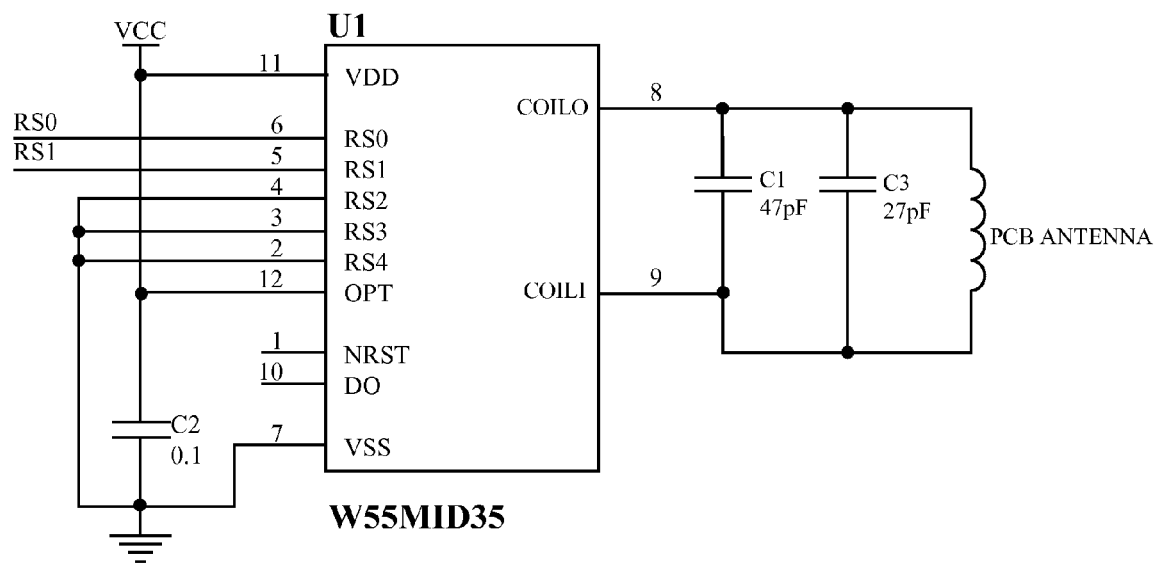
FIG. 10 is a circuitry of the RFID tag attached to each compartment of the pillbox of FIG. 1.

FIG. 10 is a circuitry of the RFID tag 35 attached to each compartment of the pillbox 100. The circuitry of the RFID tag 35 comprises an integrated circuit W55MID35 and associated peripheral circuits. The information necessary for the pillbox may be stored in the RFID tag and can be read by the RFID reader of the MCU 30.

Figure 11A:
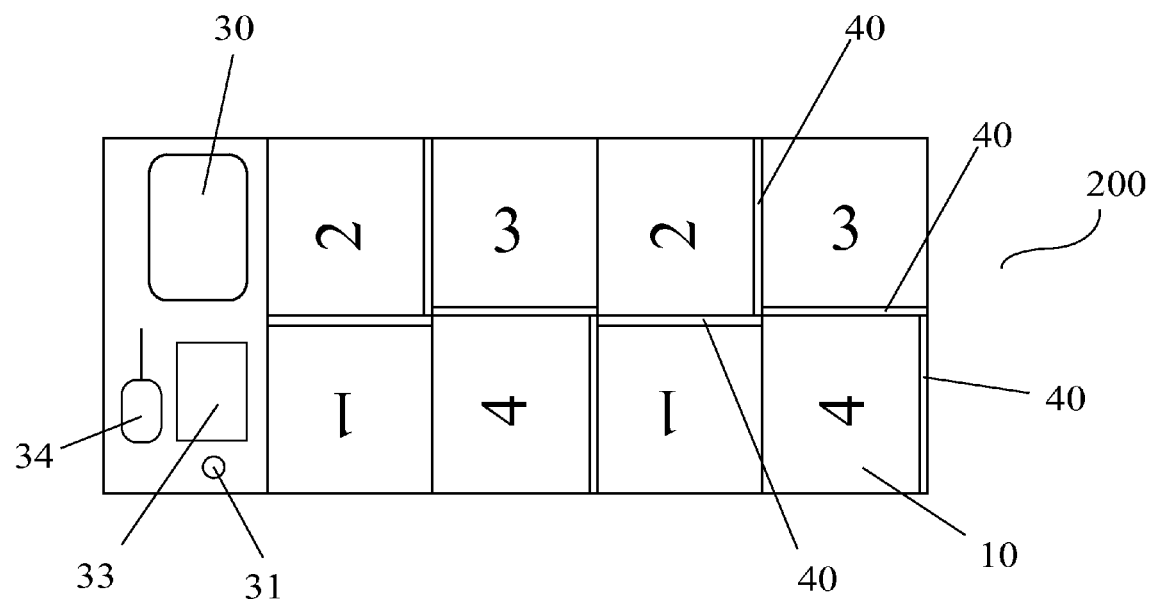
FIG. 11a is a simplified top view of a pill box a pillbox comprising a plurality of compartments constructed according to a second embodiment of the invention.
Figure 11B:
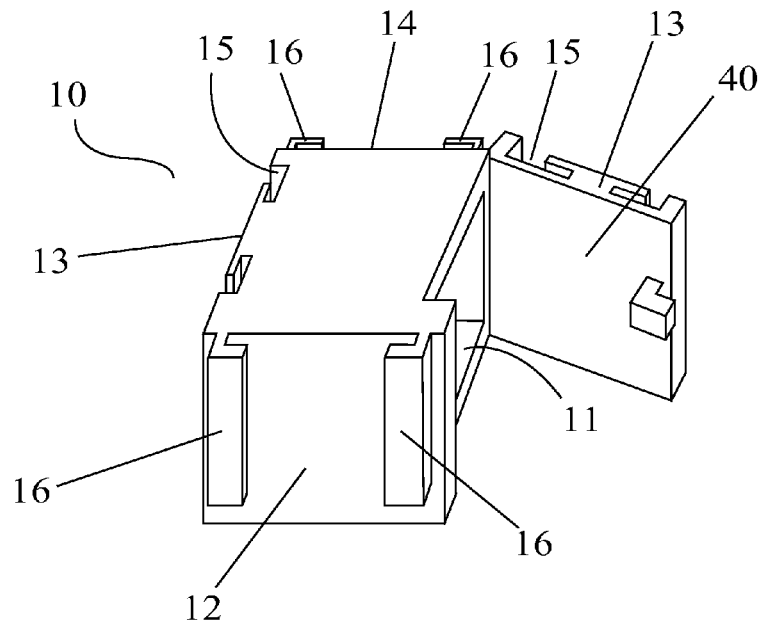

A pillbox 200 constructed consistent with a preferred first embodiment of the invention is illustrated in FIG. 11. The pillbox 200 of this embodiment is structurally same as the one shown in the first embodiment above, except the following:

the compartment 10 is constructed to have a closed top, a bottom and four side walls to define a chamber for storing the pills, wherein an opening through which the pills are accessible is formed on the side wall where the compartment is connected to the preceding compartment; and a cover of the compartment is provided as a hinged side door 40 to cover the opening formed on the side wall of the compartment.

As illustrated in FIG. 11, the side door 40 of the compartment is permitted to be opened only when the outermost compartment has been detached from the pillbox 200. This locking cover arrangement provides another economical and effective arrangement for covering the opening of the compartment while permitting to open the side door 40 only when the compartment in front of the side door 40 is removed.

Figure 12:
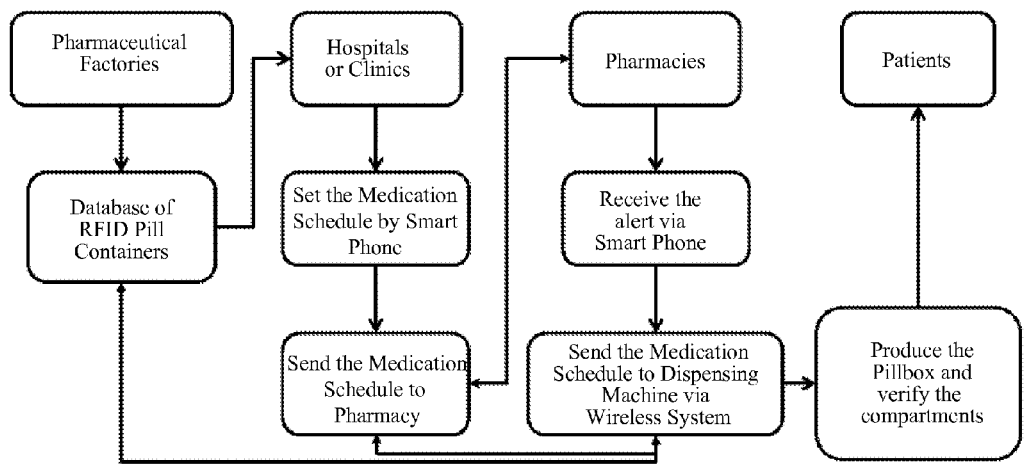
FIG. 12 is a block diagram of dispensing supply chain management system based on the pillbox of the invention.

FIG. 12 is a block diagram of dispensing supply chain management system based on the pillbox of the invention. The dispensing supply chain management system enables all interested parties including pharmaceutical factories, hospitals or clinics, pharmacies and patients via wired or wireless connection, for instance, using smart phone and internet to know the status of the pillbox of the invention. In particular, the invention provides a medication management system intended for the dispensing supply chain management shown in FIG. 12, comprising the pillbox of the invention and a server which is accessible by the interested parties using the smart phone or internet. The server contains all the data necessary for the purpose of the dispensing supply chain management.

Generally, it is assumed that a particular patient has been dispensed one or more pills and has been issued proper instructions on when and how to take the pills, thus a medication schedule is established. Namely, the doctors in the hospital or clinics provide one or more prescriptions for the patient and the medication schedule would be established according to the one or more prescriptions. These prescriptions and the medication schedule will be sent to the server and to the pharmacies. The pharmacies receives the medication schedule and transmits it to the dispensing machine via a wired or wireless system in order to dispense the prescribed pills into the plurality of compartments 10. During the dispensing, the compartments 10 will be read and verified one-by-one by reading the RFID tags 35 attached to the respective compartments, which ensures the pills are dispensed to the corresponding compartments correctly. After the dispensing process is completed, the plurality of compartments 10 would be assembled together to construct a pillbox of the invention.

The patients receive the pillbox and the relevant instructions from the doctors or the pharmacies. On the other hand, the patients are allowed to access to the system via smart phones or internet to get their own information related to the prescriptions and the medication schedule.

It is shown in FIG. 12 that the pharmaceutical factories would be able to access the dispensing supply chain management system. This provides a platform for the pharmaceutical factories to update the availability of the pills and the pill stocks. The pill containers provided by the pharmaceutical factories may be affixed with a RFID tag 54 to provide a means to trace the pills by the hospitals, clinics and pharmacies.

The dispensing supply chain management system may generate various reports showing how many patients are prescribed a drug ABC in a given period of the time, and how many patients actually take the drug ABC in that period of time, and how many patients obtain their drugs from the pharmacies X and how many patients obtain their drugs from pharmacies Y. This system also enables to keep track of the medication compliance of the patients.

Figure 13:
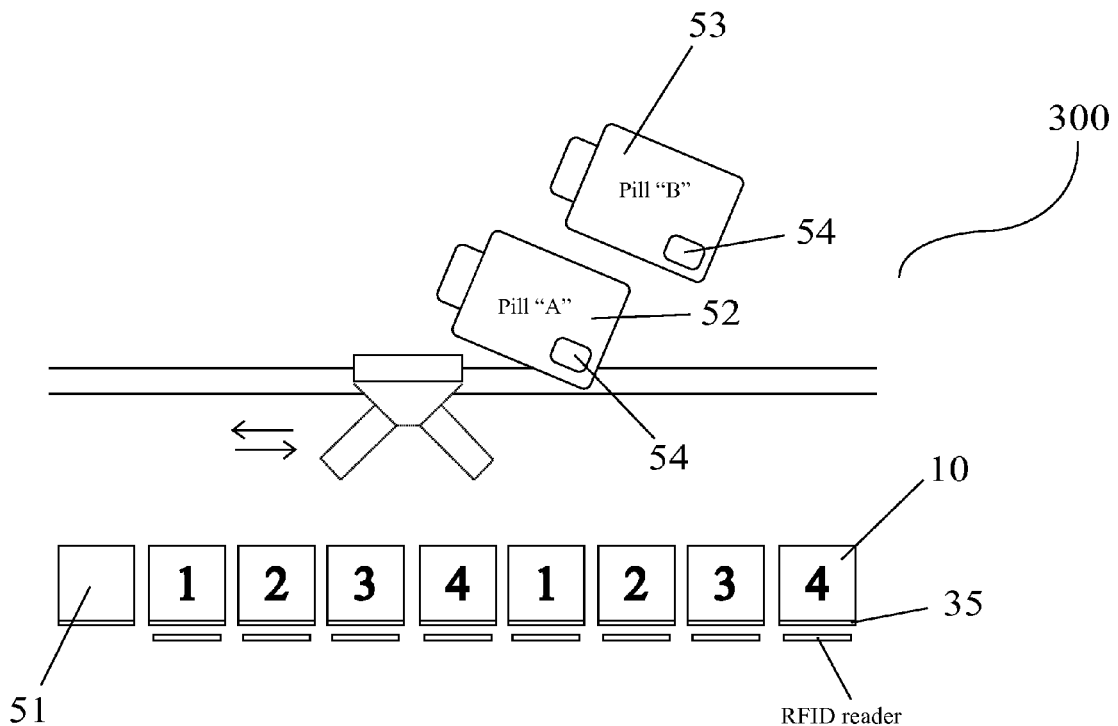
FIG. 13 is a schematic view of a medication dispensing machine according to the invention.

FIG. 13 is a schematic view of a medication dispensing machine 300 used in the pharmacies according to the invention. The dispensing machine 300 comprises a MCU with a RFID reader for reading and updating the medication schedule and verifying the compartments of the particular patient and the pill containers of the pharmaceutical factories. The dispensing machine 300 also comprises a wireless communication module connected to the MCU, enabling the pharmacies to access the dispensing machine. Proper configuration of the MCU permits the dual-pass communication between the RFID reader of the pillbox and the RFID reader of the dispensing machine 300. The operation of the medication dispensing machine 300 will be described below.

Upon the receipt of the medication schedule, the pharmacies collect the compartments which are registered through the RFID reader. Then, the compartments and the pill containers 52, 53 storing different types of pills are checked and verified through their RFID tags. The verified compartments 10 and pill containers 52, 53 will be placed in sequential order in the dispensing machine 300 which is actuated to dispense the prescribed pills into the respective compartments 10 one by one in accordance with the medication schedule. One or more pill receptacles 51 are provided to receive the pills that are redundant for constructing the pillbox.

After the compartments have been filled with the pills, they would be assembled together in sequential order according to the medication schedule to form the pillbox. Next, the medication schedule would be downloaded to the MCU of the pillbox, which is then ready to be delivered to the patient.

As discussed above, the present invention provides a pillbox that enhances the ease and convenience of taking the right medication at the right time, on the right day. The pillbox of the invention provides multiple reminder alerts to the patient to assure administration of the proper medication at the prescribed time. According to the invention, the design of the pillbox helps decrease the medication mismanagement by increasing the simplicity of patient self-administration, improves the accuracy of dispensing the pills into the pillbox, and keeps track of all medication records.

Having sufficiently described the nature of the present invention according to some preferred embodiments, the invention, however, should not be limited to the structures and functions of the embodiments and drawings. It is stated that insofar as its basic principle is not altered, changed or modified it may be subjected to variations of detail. Numerous variations and modifications that are easily obtainable by means of the skilled person's common knowledge without departing from the scope of the invention should fall into the scope of this invention.

The invention claimed is:

1. A pillbox comprising a plurality of pill receiving compartments detachably connected with one another in side-by-side relation to form a unitary structure, each of the compartments being constructed to store pills to be taken at a single predetermined time and have an opening which is covered by a cover and through which the compartment is accessible;

wherein the unitary structure is configured such that the plurality of compartments are arranged sequentially according to a medication schedule created according to a prescription for a particular patient, with the compartment storing the pills to be taken first as an outermost one, and that only the opening of the outermost compartment is permitted to remain uncovered all the time, and wherein the outermost compartment is removed from the unitary structure after the pills contained therein are taken;

wherein each of the compartments is provided at its bottom with a radio frequency identification (RFID) tag for containing and updating data associated with the pillbox, and the pillbox further comprises a microcontroller unit (MCU) with a RFID reader to process and read the data contained in the RFID tag;

wherein the data associated with the pillbox includes an ID number assigned to the respective compartment, personal data of the patient, the prescription for the patient, the medication schedule, a time when the patient is to take the pills, a time when a reminder alert is sent to the patient, and pill information including manufacturers and availability of the pills;

wherein the MCU is configured to generate a reminder alert indicating the time when the patient is to take the pills, upon reading the RFID tag of the compartment in which the pills have been taken.

2. The pillbox according to claim 1, wherein the compartment is constructed to have an opened top as the opening, a bottom, and side walls, and comprise an actuator for opening the cover and mounted on the side wall where the compartment is connected to the preceding compartment; and the cover is pivotally and openably locked to the compartment.

3. The pillbox according to claim 2, wherein each of the compartments has at least one longitudinal guiding bulge or at least one longitudinal guiding slot on the side wall where the compartment is connected to the preceding compartment and on the opposite wall thereof, respectively, and at least one longitudinal guiding slot or at least one longitudinal guiding bulge on the other two side walls, respectively, so that the guiding bulge is vertically inserted into and engages with the guiding slot to enable the connection of the adjacent two compartments.

4. The pillbox according to claim 1, wherein each of the compartments has at least one longitudinal guiding bulge or at least one longitudinal guiding slot on the side wall where the compartment is connected to the preceding compartment and on the opposite wall thereof, respectively, and at least one longitudinal guiding slot or at least one longitudinal guiding bulge on the other two side walls, respectively, so that the guiding bulge is vertically inserted into and engages with the guiding slot to enable the connection of the adjacent two compartments.

5. The pillbox according to claim 1, wherein the compartment is constructed to have a closed top, a bottom and side walls, with the opening formed in the side wall where the compartment is connected to the preceding compartment; and the cover is provided as a hinged side door to cover the opening.

6. The pillbox according to claim 1, further comprising a LED indicator operably connected to the MCU for indicating the time for the taking of the pills by the patient.

7. The pillbox according to claim 1, further comprising an acoustic output unit, particularly a beeper, operably connected to the MCU for indicating the time for the taking of the pills by the patient.

8. The pillbox according to claim 1, further comprising a vibration motor operably connected to the MCU for indicating the time for the taking of the pills by the patient.

9. The pillbox according to claim 1, further comprising a liquid crystal display operably connected to the MCU for indicating the time for the taking of the pills by the patient and indicating the compartment in which the pills are to be taken.

10. The pillbox according to claim 1, wherein the plurality of the compartments each is assigned with a corresponding ID number for a purpose of identification of the compartments.

11. The pillbox according to claim 1, further comprising a liquid crystal display operably connected to the MCU for indicating the time for the taking of the pills by the patient and indicating the compartment in which the pills are to be taken.

12. A medication management system, comprising:
a pillbox according to claim 1; and
a server which contains data associated with the pillbox and is accessible via wired or wireless connection.

13. The medication management system according to claim 12, wherein the data associated with the pillbox includes personal data of the patient, the prescription for the patient, the medication schedule, a time when the patient is to take the pills, a time when a reminder alert is sent to the patient, and pill information including manufacturers and availability of the pills.

14. A medication dispensing system, comprising:
a pillbox according to claim 1; and
a dispensing machine for dispensing the pills into the plurality of compartments according to the medication schedule and verifying the sequence of the plurality of compartments to construct the pillbox.

15. The medication dispensing system according to claim 14, wherein the dispensing machine comprises a microcontroller unit (MCU) with a RFID reader for reading and updating the data associated with the pillbox and identifying the plurality of compartments and pill containers; a communication module connected to the MCU to enable access to the dispensing machine; and a dispensing mechanism connected to the MCU for verifying and dispensing the pills from the pill containers into the plurality compartments.

16. The medication dispensing system according to claim 15, further comprising a server which is accessible via wired or wireless connection and contains data associated with the pillbox.

17. The medication dispensing system according to claim 16, wherein the data associated with the pillbox includes personal data of the patient, the prescription for the patient, the medication schedule, a time when the patient is to take the pills, a time when a reminder alert is sent to the patient, and pill information including manufacturers and availability of the pills.

18. A medication management system, comprising:
a pillbox according to claim 1; and
a server which contains data associated with the pillbox and is accessible via wired or wireless connection.

19. The medication management system according to claim 18, wherein the data associated with the pillbox includes personal data of the patient, the prescription for the patient, the medication schedule, a time when the patient is to take the pills, a time when a reminder alert is sent to the patient, and pill information including manufacturers and availability of the pills.

20. A medication management system, comprising:
a pillbox according to claim 10; and
a server which contains data associated with the pillbox and is accessible via wired or wireless connection.

21. The medication management system according to claim 20, wherein the data associated with the pillbox includes personal data of the patient, the prescription for the patient, the medication schedule, a time when the patient is to take the pills, a time when a reminder alert is sent to the patient, and pill information including manufacturers and availability of the pills.

22. A medication dispensing system, comprising:
a pillbox according to claim 1; and
a dispensing machine for dispensing the pills into the plurality of compartments according to the medication schedule and verifying the sequence of the plurality of compartments to construct the pillbox.

23. The medication dispensing system according to claim 22, wherein the dispensing machine comprises a microcontroller unit (MCU) with a RFID reader for reading and updating the data associated with the pillbox and identifying the plurality of compartments and pill containers; a communication module connected to the MCU to enable access to the dispensing machine; and a dispensing mechanism connected to the MCU for verifying and dispensing the pills from the pill containers into the plurality compartments.

24. The medication dispensing system according to claim 23, further comprising a server which is accessible via wired or wireless connection and contains data associated with the pillbox.

25. The medication dispensing system according to claim 24, wherein the data associated with the pillbox includes personal data of the patient, the prescription for the patient, the medication schedule, a time when the patient is to take the pills, a time when a reminder alert is sent to the patient, and pill information including manufacturers and availability of the pills.

26. A medication dispensing system, comprising:
a pillbox according to claim 10; and
a dispensing machine for dispensing the pills into the plurality of compartments according to the medication schedule and verifying the sequence of the plurality of compartments to construct the pillbox.

27. The medication dispensing system according to claim 26, wherein the dispensing machine comprises a microcontroller unit (MCU) with a RFID reader for reading and updating the data associated with the pillbox and identifying the plurality of compartments and pill containers; a communication module connected to the MCU to enable access to the dispensing machine; and a dispensing mechanism connected to the MCU for verifying and dispensing the pills from the pill containers into the plurality compartments.

28. The medication dispensing system according to claim 27, further comprising a server which is accessible via wired or wireless connection and contains data associated with the pillbox.

29. The medication dispensing system according to claim 28, wherein the data associated with the pillbox includes personal data of the patient, the prescription for the patient, the medication schedule, a time when the patient is to take the pills, a time when a reminder alert is sent to the patient, and pill information including manufacturers and availability of the pills.

* * * * *